(12) United States Patent
Raykov et al.

(10) Patent No.: US 10,058,591 B2
(45) Date of Patent: Aug. 28, 2018

(54) CO-ADMINISTRATION OF A PARVOVIRUS AND A CYTOKINE FOR THERAPY OF PANCREATIC CANCER

(71) Applicants: RUPRECHT-KARLS-UNIVERSITAET HEIDELBERG, Heidelberg (DE); DEUTSCHES KREBSFORSCHUNG-SZENTRUM, Heidelberg (DE)

(72) Inventors: Zahari Raykov, Heidelberg (DE); Svitlana Grekova, Heidelberg (DE); Laurent Daeffler, Heidelberg (DE); Jean Rommelaere, Heidelberg (DE); Marc Aprahamian, Limersheim (FR); Nathalia Giese, Schriesheim (DE)

(73) Assignees: Deutsches Krebsforschungszentrum, Heidelberg (DE); Ruprecht-Karls-Universitaet Heidelberg, Heidelberg (DE)

( * ) Notice: Subject to any disclaimer, the term of this patent is extended or adjusted under 35 U.S.C. 154(b) by 0 days.

(21) Appl. No.: 14/958,485

(22) Filed: Dec. 3, 2015

(65) Prior Publication Data

US 2016/0082085 A1 Mar. 24, 2016

Related U.S. Application Data (63) Continuation of application No. 14/359,001, filed as application No. PCT/EP2012/004728 on Nov. 14, 2012, now abandoned, which is a continuation of application No. 13/298,492, filed on Nov. 17, 2011, now abandoned.

(51) Int. Cl.
*A61K 38/21* (2006.01)
*A61K 35/768* (2015.01)
*A61K 45/06* (2006.01)

(52) U.S. Cl.
CPC .......... *A61K 38/217* (2013.01); *A61K 35/768* (2013.01); *A61K 45/06* (2013.01)

(58) Field of Classification Search
CPC .... A61K 38/217; A61K 35/768; A61K 45/06; A61K 2300/00
See application file for complete search history.

(56) References Cited

U.S. PATENT DOCUMENTS

| | | | | |
|---|---|---|---|---|
| 8,414,883 | B2 * | 4/2013 | Rommelaere | A61K 31/4188 424/93.2 |
| 2010/0331815 | A1 * | 12/2010 | Alt | A61K 38/21 604/507 |
| 2011/0033425 | A1 | 2/2011 | Raykov et al. | |
| 2012/0213734 | A1 | 8/2012 | Kiprijanova et al. | |

FOREIGN PATENT DOCUMENTS

| | | | |
|---|---|---|---|
| WO | WO 97/41884 | | 11/1997 |
| WO | WO99/18799 | * | 4/1999 |
| WO | WO 99/18799 A1 | | 4/1999 |
| WO | WO 2011/113600 A1 | | 9/2011 |

OTHER PUBLICATIONS

Grekova, S.P. et al. Interferon-gamma improves the vaccinatoin potential of oncolytic parvovirus H-1PV for the treatment of peritoneal carcinomatosis in pancreatic cancer. Cancer Biology and Therapy, 2011, vol. 12, p. 888-895.*
Corresponding International Search Report dated Mar. 25, 2013 (three (3) pages).
Svitlana Grekova et al., "Immune Cells Participate in the Oncosuppresive Activity of Parvovirus H-1PV and are Activated as a Result of Their Abortive Infection with this Agent", Cancer Biology & Therapy, vol. 10, Issue 12, Dec. 15, 2010, pp. 1280-1289, XP-002693556.
Jean Rommelaere et al., "Oncolytic Parvoviruses as Cancer Therapeutics", Cytokine & Growth Factors Reviews, vol. 21, Issue 2-3, Apr. 1, 2010, pp. 185-195, XP 27066640.
Svitlana P. Grekova et al., "Interferon y Improves the Vaccination Potential of Oncolytic Parvovirus H-1PV for the Treatment of Peritoneal Carcinomatosis in Pancreatic Cancer", Cancer Biology & Therapy, vol. 12, issue 10, Nov. 15, 2011, pp. 888-895, XP002693555.
International Preliminary Report on Patentability dated May 20, 2014 (five (5) pages).
Amanda Corcoran et al., Impaired Gamma Interferon Responses Against Parvovirus B19 By Recently Infected Children, Journal of Virology (2000) vol. 74, No. 21, p. 9903-9910.
R. Franssila et al., T Helper Cell-Mediated Interferon-Gamma Expression After Human Parvovirus B19 Infection: Persisting VP2-Specific and Transient VP1u-Specific Activity, British Society of Immunology, Clinical and Experimental Immunology (2005) vol. 142, p. 53-61.
Jorg R. Schlehofer et al., Parvoviruses Are Inefficient in Inducing Interferon-β, Tumor Necrosis Factor-a, or Interleukin-6 In Mammalian Cells, Med Microbiol Immunol (1992) vol. 181, p. 153-164.
Angelova, A. L. et al., Improvement of Gemcitabine-Based Therapy of Pancreatic Carcinoma by Means of Oncolytic Parvovirus H1PV. Clin. Cancer Res., 2009, vol. 15, p. 511-519.
Nabioullin, R. et al., Interleukin-10 is a potent inhibitor of tumor cytotoxicity by human monocytes and alveolar macrophages. J. Leukocyte Biology, 1994, vol. 55, p. 437-442.
Ahmedin Jemal et al., Cancer Statistics, 2009, Cancer Journal for Clinicians, pp. 1-40.
Matthew H.G. Katz et al., "Current Status of Adjuvant Therapy for Pancreatic Cancer", 2010, The Oncologist, pp. 1-9.
David H. Kirn et al., "Replicating Viruses as Selective Cancer Therapeutics", 1996, Molecular Medicine Today, pp. 519-527.

(Continued)

*Primary Examiner* — Robert S Landsman
*Assistant Examiner* — Bruce D. Hissong
(74) *Attorney, Agent, or Firm* — Crowell & Moring LLP (57) ABSTRACT

The present invention relates to a combination of a parvovirus and a cytokine, preferably $IFN_y$, for use in treating pancreatic cancer, in particular a terminal stage of this disease.

2 Claims, 5 Drawing Sheets

(56) References Cited

OTHER PUBLICATIONS

Xue Qing Lun et al., "Efficacy of Systemically Administered Oncolytic Vaccinia Virotherapy for Malignant Gliomas Is Enhanced by Combination Therapy with Rapamycin or Cyclophosphamide", 2009, Cancer Therapy: Preclinical, www.aacrjournals.org pp. 2777-2788.

Jan J. Cornelis et al., "Autonomous Parvovirus Vectors", 2000, Institute of Applied Tumor Virology, German Cancer Research Center, Department of Virology Institute Pasteur, Institute of Biochemistry, University of Mainz, twenty-one (21) pages.

U.S. Appl. No. 15/229,276, filed Aug. 5, 2016.

* cited by examiner

CO-ADMINISTRATION OF A PARVOVIRUS AND A CYTOKINE FOR THERAPY OF PANCREATIC CANCER

This application is a Continuation of U.S. patent application Ser. No. 14/359,001, filed May 16, 2014, which is a national stage entry under 35 U.S.C. § 371 of PCT International Application No. PCT/EP2012/004728, filed Nov. 14, 2012, which claims priority under 35 U.S.C. § 120 to U.S. patent application Ser. No. 13/298,492, filed Nov. 17, 2011, the entire disclosures of all of which are expressly incorporated by reference herein.

The present invention relates to a combination of a parvovirus and a cytokine, preferably IFN$_\gamma$, for use in treating pancreatic cancer, in particular a terminal stage of this disease.

Pancreatic cancer is an aggressive malignancy with one of the worst outcomes among all cancers. For all stages combined, the 5-year relative survival rate is only 5% (1). The radical surgery (Whipple's operation) is the only curative option in this aggressive tumor but can be offered to less than 20% of pancreatic ductal adenocarcinoma cancer (PDAC) patients. Chemotherapy can be used as adjuvant to surgery or in advanced stage pancreatic cancer where, in a small group of patients, it offers real benefit in terms of survival and quality of life (2). Nevertheless, the therapeutic options for PDAC patients, especially these with peritoneal carcinosis, are lacking.

Novel virus-based anticancer therapies involve the use of viruses either as replicating oncolytic agents, or as recombinant vectors for gene transfer (3). The autonomous parvoviruses MVMp and H-1 belong to a group of small (~5 kb) non-integrating single-stranded DNA viruses. Their oncotropic and oncotoxic properties make them promising candidates for both types of applications (4). Recently it could be demonstrated that applying H-1PV as monotherapy or as second-line treatment after gemcitabine chemotherapy, caused the reduction of tumor growth, prolonged the survival of rats bearing pre-established pancreatic tumors and led to the suppression of metastases (5). Furthermore, it was found that immunological mechanisms are involved in the anticancer activity of H-1PV with a strong correlation between the therapeutic effect of the virus and IFN-$\gamma$ expression in the draining lymph nodes of pancreatic tumors (6).

Despite the impressive results achieved the anticancer efficacy of the most promising parvovirus candidates for human clinical applications (including H-1PV) needs to be improved, e.g., as regards the extension of life span after diagnosis and as regards particular tumors like pancreatic tumors.

Therefore, it is the object of the present invention to provide means for an improved parvovirus-based therapy.

According to the invention this is achieved by the subject matters defined in the claims. Oncolytic viruses with their capacity to specifically replicate in and kill tumor cells emerged as a novel class of cancer therapeutics. Rat oncolytic parvovirus (H-1PV) was used to treat different types of cancer in preclinical settings and was lately successfully combined with standard gemcitabine chemotherapy in treating pancreatic ductal adenocarcinoma in rats (PDAC). The experiments resulting in the present invention are based on the idea that the therapeutic properties of H-1PV can be boosted with IFN$_\gamma$ for the treatment of late incurable stages of PDAC like peritoneal carcinosis. Rats bearing established orthotopic pancreatic carcinomas with peritoneal metastases were treated with a single intratumoral (i.t.) or intraperitoneal (i.p.) injection of 5×10$^8$ plaque forming units of H-1PV with or without concomitant IFN$_\gamma$ application. Intratumoral injection proved to be more effective than the intraperitoneal route in controlling the growth of both the primary pancreatic tumors and peritoneal carcinosis, accompanied by migration of virus from primary to metastatic deposits. Concomitant i.p. treatment of H-1PV with recIFN$_\gamma$ resulted in improved therapeutic effect yielding an extended animal survival, compared to i.p. treatment with H-1PV alone. IFN$_\gamma$ application enhanced the H-1PV-induced peritoneal macrophage and splenocyte responses against tumor cells while causing a significant reduction in the titers of H1-PV-neutralising antibodies in ascitic fluid. Thus, IFN$_\gamma$ co-application together with H-1PV might be considered as a novel therapeutic option to improve the survival of PDAC patients with peritoneal carcinosis.

BRIEF DESCRIPTION OF THE DRAWINGS

(B) Peritoneal macrophages (5×10$^5$/well) from the same groups of rats were cocultured or not with 1×10$^5$ HA-RPC cells at a 5:1 ratio in 48-well plates and the release of interleukins −10 and −12 was measured by ELISA. Mean cytokine ratios and standard deviations are presented.

(C) Single cell suspensions of rat splenocytes were labeled with CFSE, plated in 24 well plates at 1×10$^6$ cells/well and cocultured or not with 2×10$^5$ HA-RPC cells at a 5:1. Ratio. 48 hrs later cells were harvested and processed for FACS analysis of proliferation.

All data were median from three animals from triplicate wells. Differences were considered significant at p values below 0.05.

(B) Two animals per group were sacrificed 1 week after H-1PV and/or IFN$_\gamma$ treatments. Total RNA was extracted from visible tumors and metastases, converted to cDNA and subjected to RT-PCRs to evaluate the presence of H-1PV DNA/unspliced mRNA and b-actin transcripts, using respective primers. The abbreviations for the route and type of treatment are indicated on the figure. The source of the material (Tumour or Metastasis) is indicated in superscript.

Macrophages were isolated from the peritoneal cavity of the H-1PV and H-1PV+IFNy intraperitoneally injected rats, plated at $5\times10^5$/well in 48 well plates and cocultured or not with $1\times10^5$ HA-RPC cells. The ratios of TNFα and IL-10 in supernatants were determined 24 hrs. later by ELISA.

(B) Two groups of metastasis bearing rats were treated with two intraperitoneal injections of H-1PV ($3\times10^8$ pfu/injection per animal) spanning four weeks between them, with or without intermediate recIFN i.p. inoculation. Titers of αH-1PV in ascitic fluids were determined 10-30 days after the second H-1PV i.p. injection and expressed as indicated above.

Thus, the present invention provides a combination of a parvovirus and a cytokine, preferably a parvovirus and a cytokine as separate entities, e.g. in separate containers, for use in treating pancreatic cancer.

This combination of compounds is particularly useful for treating a terminal stage of pancreatic cancer. "Terminal stage" means a disease that cannot be cured or adequately treated and that is reasonably expected to result in the death of the patient within a relatively short period of time, e.g. within some weeks or months. The combination of compounds is suitable for treating in particular an incurable stage, like peritoneal carcinosis. Peritoneal carcinosis represents the advanced evolutive stage of several tumors that develop into abdominal organs, such as colon, ovary, appendix, stomach, pancreas and liver. When the disease increases, the tumoral cells reach and affect the membrane covering the same organs (visceral peritoneum). Once this "barrier" has been passed, the affected cells are able to move into the abdominal cavity, carried by the peritoneal fluid. Even in mesothelioma cases that affect directly the peritoneum, tumoral cells can break off the membrane and fall into the peritoneal fluid. The tumoral cells present into the liquid can die or survive feeding on substances contained in the same liquid. These cells tend to accumulate in those points of greater liquid readsorption, creating agglomerates that grow more and more, spreading into the whole abdomen and originating the carcinosis.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort. Rodent parvoviruses are preferred. Particularly preferred are the following rodent parvoviruses: H1 (H1-PV), LuIII, Mouse minute virus (MMV), Mouse parvovirus (MPV), Rat minute virus (RMV), Rat parvovirus (RPV) and Rat virus (RV).

Patients treatable by the combination of agents according to the invention include humans as well as non-human animals. Examples of the latter include, without limitation, animals such as cows, sheep, pigs, horses, dogs, and cats.

As used herein, the term "cytokine" relates to a category of signalling molecules that are used extensively in cellular communication. They comprise proteins, peptides, or glycoproteins. The term cytokine encompasses a large family of polypeptide regulators that are produced widely throughout the body by cells of diverse embryological origin. The action of cytokines may be autocrine, paracrine, and endocrine. All cytokines are critical to the development and functioning of both the innate and adaptive immune response. They are often secreted by immune cells that have encountered a pathogen, thereby activating and recruiting further immune cells to increase the system's response to the pathogen. Relying on the assays shown in Examples 2 to 5 the person skilled in the art is in a position to select cytokines that show beneficial effects when administrated according to the present invention.

Preferably, the cytokine of the present invention is an interferon. All interferons (IFNs) are natural cell-signalling proteins produced by the cells of the immune system of most vertebrates in response to challenges such as viruses, parasites and tumor cells. Interferons are produced by a wide variety of cells in response to the presence of double-stranded RNA, a key indicator of viral infection. Interferons assist the immune response by inhibiting viral replication within host cells, activating natural killer cells and macrophages, increasing antigen presentation to lymphocytes, and inducing the resistance of host cells to viral infection. All interferons in general have several effects in common and, accordingly, the results obtained by use of $IFN_{\gamma}$ in combination with a parvovirus, preferably H1-PV, might apply to further interferons. Interferons are antiviral and possess antioncogenic properties, macrophage and natural killer cell activation, and enhancement of major histocompatibility complex glycoprotein classes I and II, and thus presentation of foreign (microbial) peptides to T cells. The production of interferons is induced in response to microbes such as viruses and bacteria and their products (viral glycoproteins, viral RNA, bacterial endotoxin, bacterial flagella, CpG sites), as well as mitogens and other cytokines, for example interleukin 1, interleukin 2, interleukin-12, tumor necrosis factor and colony-stimulating factor, that are synthesised in the response to the appearance of various antigens in the body. Their metabolism and excretion take place mainly in the liver and kidneys. They rarely pass the placenta but they can cross the blood-brain barrier.

There are three major classes of interferons that have been described for humans:

(a) Interferon type I: The type I interferons present in humans are IFN-α, IFN-β and IFN-ω

(b) Interferon type II: In humans this is $IFN_{\gamma}$.

(c) Interferon type III: Signal through a receptor complex consisting of IL1OR2 (also called CRF2-4) and IFNLR1 (also called CRF2-12)

In a preferred embodiment of the present invention, the interferon is interferon-$_{\gamma}$ ($IFN_{\gamma}$).

Preferably, for the therapeutic use of the present invention the parvovirus and the cytokine are present in an effective dose and combined with a pharmaceutically acceptable carrier. "Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

An "effective dose" refers to amounts of the active ingredients that are sufficient to affect the course and the severity of the tumor, leading to the reduction or remission of such pathology. An "effective dose" useful for treating and/or preventing these diseases may be determined using methods known to one skilled in the art (see for example, Fingl et al., The Pharmocological Basis of Therapeutics, Goodman and Gilman, eds. Macmillan Publishing Co., New York, pp. 1-46 ((1975)).

Preferred doses of the parvovirus are in the range of about $10^8$ to $10^9$ pfu (single injection) in rats and of the cytokine, in particular $IFN_\gamma$, in the range of about $10^5$ to $10^6$ IU (single injection). For humans the preferred effective dose of the parvovirus is approximately $10^{11}$ pfu and of the cytokine (e.g. $IFN_\gamma$) about $2\times10^6$ to $10^8$ IU.

Additional pharmaceutically compatible carriers can include gels, bioasorbable matrix materials, implantation elements containing the therapeutic agent, or any other suitable vehicle, delivery or dispensing means or material(s).

Administration of the compounds may be effected by different ways, e.g. by intravenous, intraperetoneal, subcutaneous, intramuscular, topical or intradermal administration. The route of administration, of course, depends on the kind of therapy and the kind of compounds contained in the pharmaceutical composition. The dosage regimen of the parvovirus and the cytokine is readily determinable within the skill of the art, by the attending physician based on patient data, observations and other clinical factors, including for example the patient's size, body surface area, age, sex, the particular parvovirus to be administered, the time and route of administration, the tumor type and characteristics, general health of the patient, and other drug therapies to which the patient is being subjected.

If the parvovirus comprises infectious virus particles with the ability to penetrate through the blood-brain barrier, treatment can be performed or at least initiated by intravenous injection of the parvovirus, e.g., H1 virus. As another specific administration technique, the parvovirus (virus, vector and/or cell agent) containing composition can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus containing composition to be injected locally at various times without further surgical intervention. The parvovirus or derived vectors containing composition can also be injected into the tumor by stereotactic surgical techniques or by neuronavigation targeting techniques. Administration of the parvovirus containing compositions can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvovirus containing composition is from an implanted article constructed and arranged to dispense the parvovirus containing composition to the desired cancer tissue. For example, wafers can be employed that have been impregnated with the parvovirus containing composition, e.g., parvovirus H1, wherein the wafer is attached to the edges of the resection cavity at the conclusion of surgical tumor removal. Multiple wafers can be employed in such therapeutic intervention. Cells that actively produce the parvovirus, e.g., parvovirus H1, or H1 vectors, can be injected into, the tumor, or into the tumoral cavity after tumor removal.

Preferably, the parvovirus and the cytokine are administered as separate compounds. The administration of the cytokine, when administered separately, can be accomplished in a variety of ways. A preferred route of administration of the parvovirus is intratumoral administration. A preferred route of administration of the cytokine is intraperitoneal administration. The combination of both routes of administration shows synergistic effects.

The therapeutic efficacy of the combination of compounds according to the present invention can be further improved by co-administration of an immunosuppressive agent like rapamycin or cyclophosphamide.

The below examples explain the invention in more detail.

EXAMPLE 1

Materials and Methods (A) Cells and Reagents

Human pancreatic carcinoma cell lines from primary (Panc-1, MiaPaCa-2, BxPC-3) or metastatic (Capan 1, T3M4, AsPC-1, Colo357) tumors, were obtained from ATCC (Manassas, Va.) and grown in RPMI 1640 medium supplemented with 10% fetal calf serum (FCS). The HA-RPC cell line (ATCC, LGC Standards, Wesel Germany) derived from a chemically induced pancreatic ductal adenocarcinoma in Lewis rats was grown in DMEM supplemented with 10% FCS. Human NB324K cells (ATCC, LGC Standards, Wesel Germany) used for cytotoxicity protection assays were cultured in MEM medium with 5% FCS. All media were supplemented with penicillin (100 U/ml) and streptomycin (100 µg/ml). Lyophilized recombinant rat and human $IFN_\gamma$ were obtained from Biomol GMBH (Hamburg, Germany) and reconstituted in sterile deionized water. The mouse monoclonal antibody clone DB-1 with specificity against murine $IFN_\gamma$ ($\alpha IFN_\gamma$) was produced in bulk amount by NatuTec GmbH (Frankfurt, Germany). Where indicated, in some experiments cells were stimulated using LPS at final concentration of 5 µg/ml.

For the isolation of peritoneal macrophages rats received an i.p. injection of 4 ml of 4% Thioglycolate solution in PBS three days before sacrifice. After sacrificing the animals, 40 ml of sterile PBS were instilated in the peritoneal cavity and recovered using a syringe. The cells were collected by centrifugation and plated in DMEM containing 10% FCS and antibiotics.

Peripheral blood mononuclear cells (PBMC) were isolated from the heparinized blood of randomly selected healthy donors by differential centrifugation over Histopaque (Sigma) and cultured in RPMI with 10% FCS and antibiotics. Peripheral blood macrophages were enriched by adherence to plastic surface. Buffy coats were obtained from the blood bank of IKTZ Heidelberg.

(B) Virus-Neutralizing Antibody Detection

Serial dilutions of the sera of experimental animals were made in MEM and mixed with an equal volume of H-1PV virus suspension (corresponding to $2\times10^4$ pfu/well). After incubation for 30 min. at 37° C., the mixture was inoculated onto NB324K cells plated in 96-well plates ($2\times10^3$ cells/well). The cell survival rates were assessed after 72 h using a MTT (3-(4,5-dimethylthiazolyl-2)-2,5-diphenyltetrazolium bromide) assay.

(C) Semi-Quantitative RT-PCR

For RT-PCR total RNA was extracted from pancreatic tumors or metastatic nodules of treated animals, reverse transcribed into cDNA, and PCRs for H-1PV and β-actin were performed using previously described primer sequences and conditions (6).

(D) ELISA

Measurement of rat $TNF_\gamma$; IL-10, IL-12 and human TNFα release was done using commercially available ELISA kits from eBioscience (Frankfurt, Germany) as described by manufacturer.

(E) FACS Determination of Splenocytes' Proliferation Index

Rat spleens were pressed against a mesh to obtain single cell suspensions and splenocytes were adjusted to a concentration of $5\times10^6$/ml in PBS. The stock 5 mM CFSE solution was diluted at 1/1000 in PBS (a final concentration of 5 μM), added to lymphocytes pellet and mixed rapidly. After incubation for 5 minutes at room temperature 10 volumes of PBS containing 5% FSC were added and the cells were centrifuged. Washes in PBS/FCS were repeated 3 times. Labeled splenocytes were co-cultured with HA-RPC cells or alone as a control. After 72 h of incubation, cells were collected, washed and measured for CFSE fluorescence using FACSCalibur (BD, Calif., USA). The proliferation index was calculated based on the level of reduction in fluorescence intensity of the cultures.

(F) Animal Studies

The orthotopic rat model using HA-RPC cells has been previously described (5). For the induction of metastasis a cell suspension was prepared in phosphate-buffered saline (PBS) out of subcutaneous tumors preformed by implantation of HA-RPC cells and injected intraperitoneally to Lewis rats at $3\times10^6$ cells in 500 μl per. animal.

Rat $recIFN_\gamma$ was injected in 3 consecutive weeks at 30 000 UI/week i.p. in a 100 μl volume for a total dose of 90 000 UI/animal. The $\alpha IFN_\gamma$ antibody was applied at the same times at 0.8 mg/animal for a total dose of 2.4 mg. Ascitic fluid was obtained using a peritoneal puncture under aerosol anesthesia at the time before animal sacrifice.

(G) Statistical Methods

Means and standard deviations were calculated from at least three animals in triplicate wells in vitro experiments. Statistical differences were assessed using Student's t test and Wilcoxon test. For in vivo mortality data assessment, experimental groups were compared with log-rank test.

EXAMPLE 2

RecIFNy Contributes to the Immunomodulating Anticancer Effect of H-1PV

Figure 1:
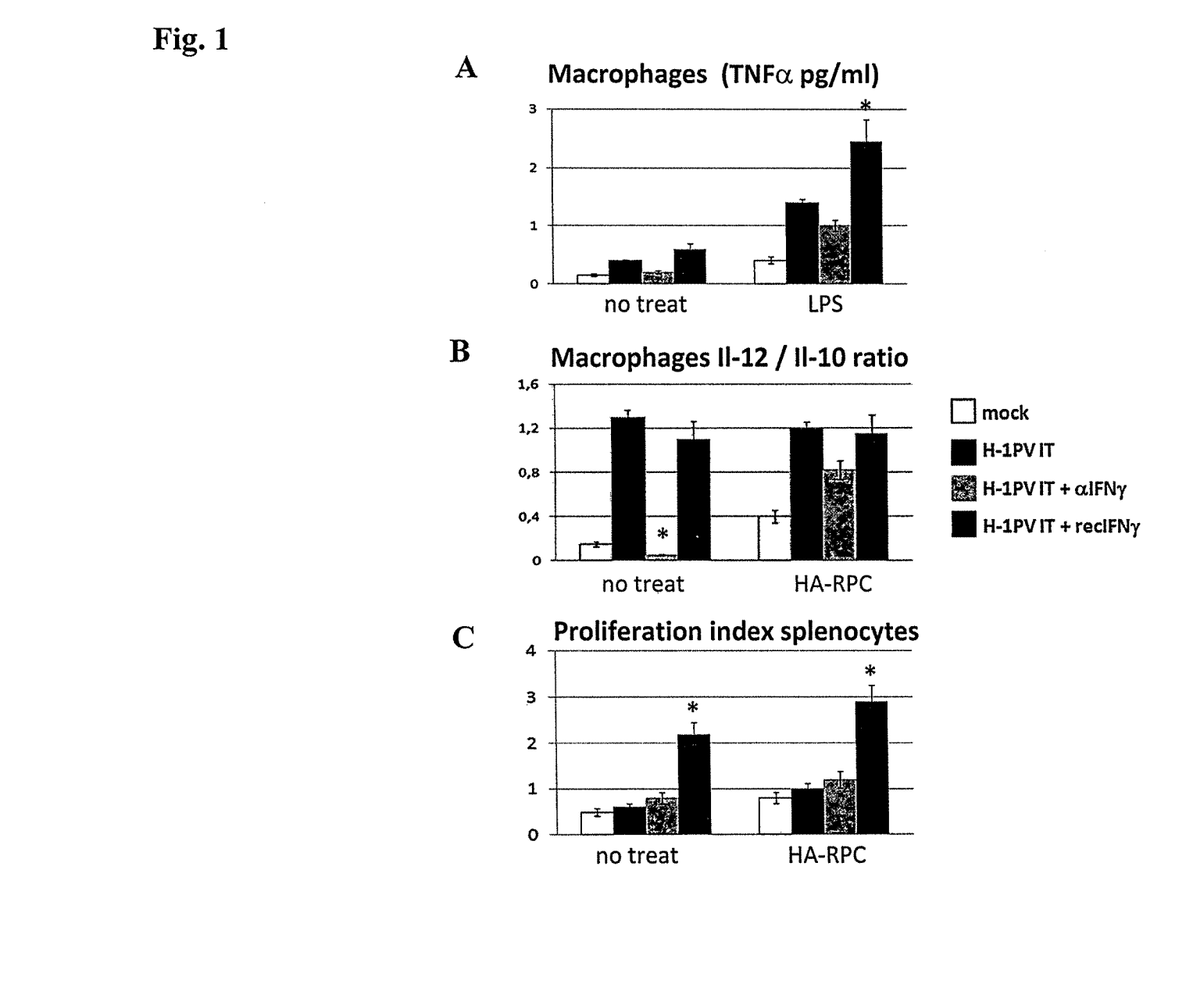
FIG. 1: Impact of IFN$_\gamma$ addition or depletion on H-1PV immunomodulating activity (A) Macrophages were isolated from the peritoneal cavity of four groups (n32 3) of tumor bearing Lewis rats treated either with PBS (mock) or with an intratumoral injection of 5×10$^8$ pfu/rat of H-1PV (H-1PV IT) combined either with an antibody against IFN$_\gamma$ (H-1PV IT+αIFN$_\gamma$) or recombinant IFN$_\gamma$ (H-1PV IT+recIFN$_\gamma$). Cells were plated in 48-well plates at a density of 5×10$^5$ cells per well and stimulated or not with LPS. TNFα production in the supernatants was measured 24 hrs. later by ELISA. Average values and standard deviations are shown.

As a first step the potential impact of interferon-γ on the immunomodulating features of parvovirus H-1PV in pancreatic cancer was established. Therefore, H-1PV was applied in tumors raised orthotopically through injection of HA-RPC cells in the pancreatic tail of three groups of rats using a PBS-treated group as control. Virus treatment was also combined either with intraperitoneal recombinant rat interferon ($recIFN_\gamma$) or with a neutralizing antibody against it ($\alpha IFN_\gamma$). Three days later animals were sacrificed to perform immunological profiling of splenocytes and peritoneal macrophages. The cells were cultured for 48 hours either alone (no treat), together with HA-RPC rat pancreatic cancer cells (the cell line used for initiating the tumors) or LPS. Different parameters related to the anticancer immune response, like the production of TNFα (FIG. 1A), the IL-12/IL-10 ratio (FIG. 1B) of cytokines released by macrophages, as well as the proliferation capacity of splenocytes (FIG. 1C) were analyzed. The supernatants of macrophages isolated from rats, in H-1PV was combined with $recIFN_\gamma$ contained up to 1 ng TNFα, compared to those obtained from animals treated virus only. The lowest levels of TNFα release were measured either in the non-treated mock (0.2 and 0.5 ng) or when rats were treated with a neutralizing antibody against interferon gamma (0.3 and 1 ng). A similar pattern of effects of $recIFN_\gamma$ and $\alpha IFN_\gamma$ was detected when comparing the IL-12/IL-10 ratios of the different macrophage cultures. In addition, the combination of H-1PV with recombinant interferon gamma caused a significant twofold increase in the proliferative potential of splenocytes both spontaneously and in the presence of tumor cells.

These data pointed that H-1PV application alone can activate peritoneal macrophages or combined with $recIFN_\gamma$ i.p. introduction could change the activation status of immune cells both in spleen and in the peritoneal cavity leading to predominance of immuno-stimulatory cytokines (TNFα, IL-12) over the immunosuppressive factors (IL-10). The decrease of the above-mentioned immunological parameters upon depletion of $IFN_\gamma$, especially in the case of peritoneal macrophages, confirmed our assumption that this cytokine plays a role in stimulating the innate immune system as part of the immunomodulating effect of oncolytic H-1PV.

EXAMPLE 3

Figure 2:
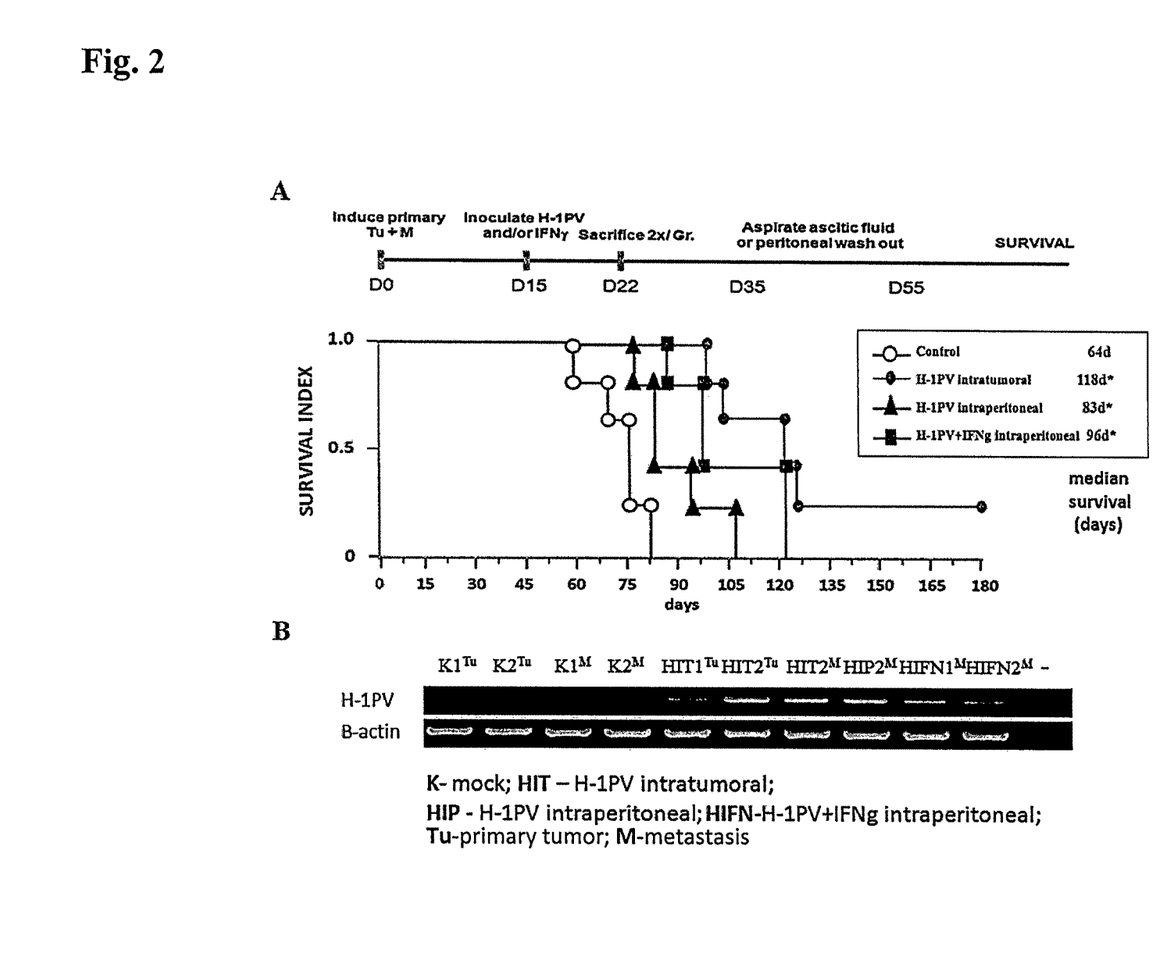
FIG. 2: Therapeutic effects of H-1PV+IFN$_\gamma$ combination and virus distribution (A) Lewis rats (n=28) bearing simultaneously induced orthotopic tumors and peritoneal metastases were divided into four groups (n=7) and either left untreated (Control), inoculated i.t. (H-1PV intratumoral) or i.p (H-1PV intraperitoneal) with H-1PV in the absence or presence of recIFNy (H-1PV+IFN$_\gamma$ intraperitoneal). After the sacrifice of two animals 1 week after treatment, the survival of five rats from each group was followed up to six months after tumor induction when animals were sacrificed. Median values were considered significant at p values below 0.05.

$RecIFN_\gamma$ Improves the Therapeutic Potential of H-1PV for the Treatment of PDAC Peritoneal Carcinosis Since the results obtained were encouraging a combination of recombinant $IFN_\gamma$ and H-1PV parvovirus was used for the treatment of one of the most lethal complications of pancreatic cancer in humans, namely the spread of the tumor to the peritoneal cavity. To mimic this situation tumors both in the pancreas and in the peritoneal cavity of Lewis rats were induced. Two weeks later, the rats were randomly divided into four groups, in which H-1PV was applied through two different routes (intratumoral or intraperitoneal). In one group the virus i.p. inoculation was combined with $recIFN_\gamma$ using the same route (FIG. 2A protocol). Animal survival was followed (FIG. 2A) confirming that H-1PV intratumoral injection was still most effective to protect rats against PDAC with two animals remaining tumor free more than six months after treatment (5). H-1PV could significantly improve the survival of rats upon peritoneal application compared to the control group but was still less effective in comparison to the i.t. route. Notably, the combination with $recIFN_\gamma$ could significantly improve the effect of the virus extending the median survival from 83 to 96 days (FIG. 2A).

Two animals per group were sacrificed one week after treatment to analyze virus presence by RT-PCR (FIG. 2B). The distribution of viral DNA signals showed that (i) the virus could migrate from the primary tumor after intratumoral application (HIT$^{Tu}$) to metastasis (HIT$^M$) in the peritoneal cavity, (ii) it can infect metastasis upon intraperitoneal inoculation (HIP$^M$), and (iii) that upon i.p. combination with H-1PV IFN$_Y$ does not change significantly the virus levels in metastases (compare HIP$^M$ and HIFN$^M$).

Figure 3:
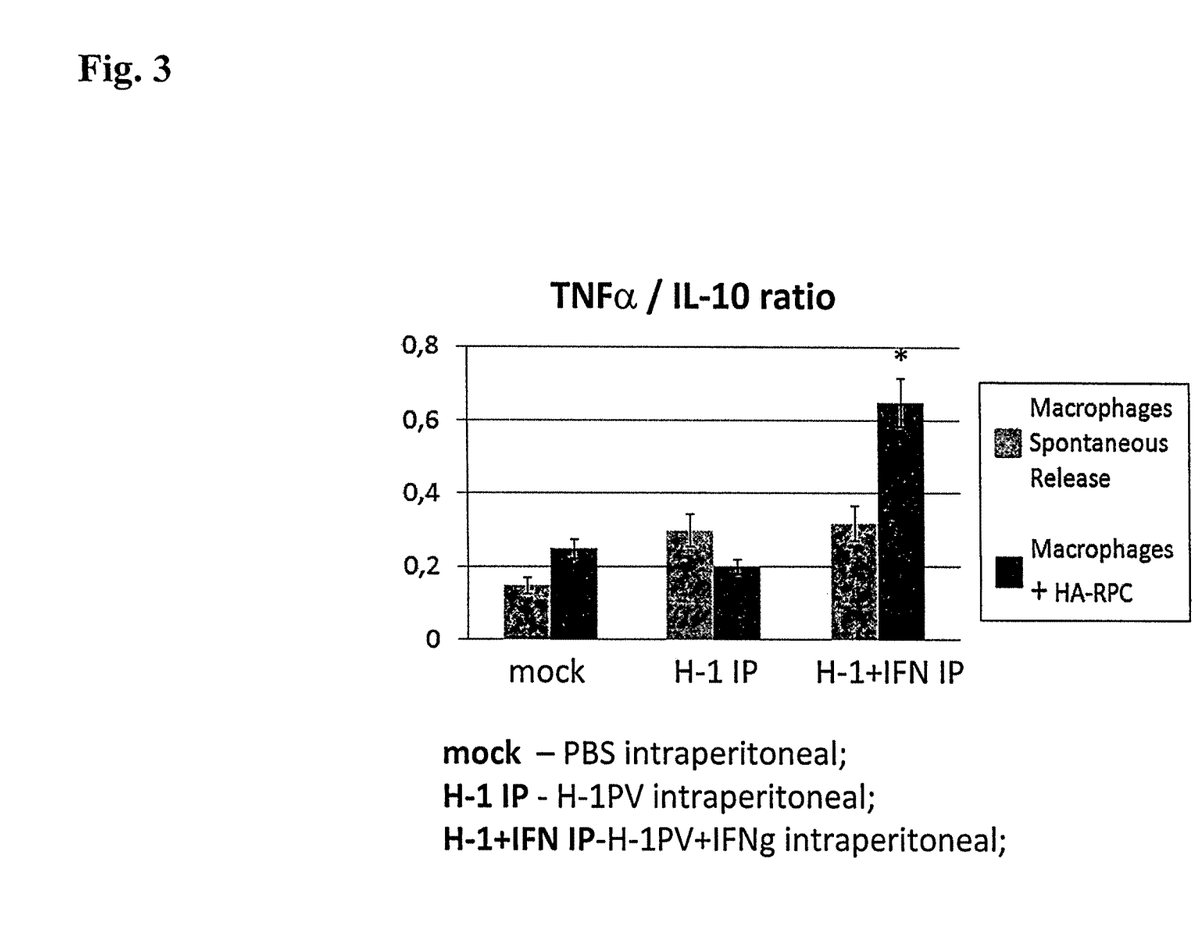
FIG. 3: Macrophage activation after H-1PV+IFNy combined treatment

Isolation of peritoneal macrophages from mock, H-1PV or H-1PV with IFN$_Y$ intraperitoneally treated rats showed that the ratio between TNFα and IL-10 produced was significantly increased in the presence of recombinant IFN$_Y$ when macrophages were cocultured with HA-RPC cells, speaking in favor of phagocytes' activation (FIG. 3).

In conclusion, intratumoral application of H-1PV seems to have a superior effect compared to intraperitoneal inoculation for the treatment of PDAC. In case intraperitoneal inoculations of the virus are performed at the stage of advanced metastatic disease, a combination with IFNy can be very favorable.

EXAMPLE 4

Figure 4:
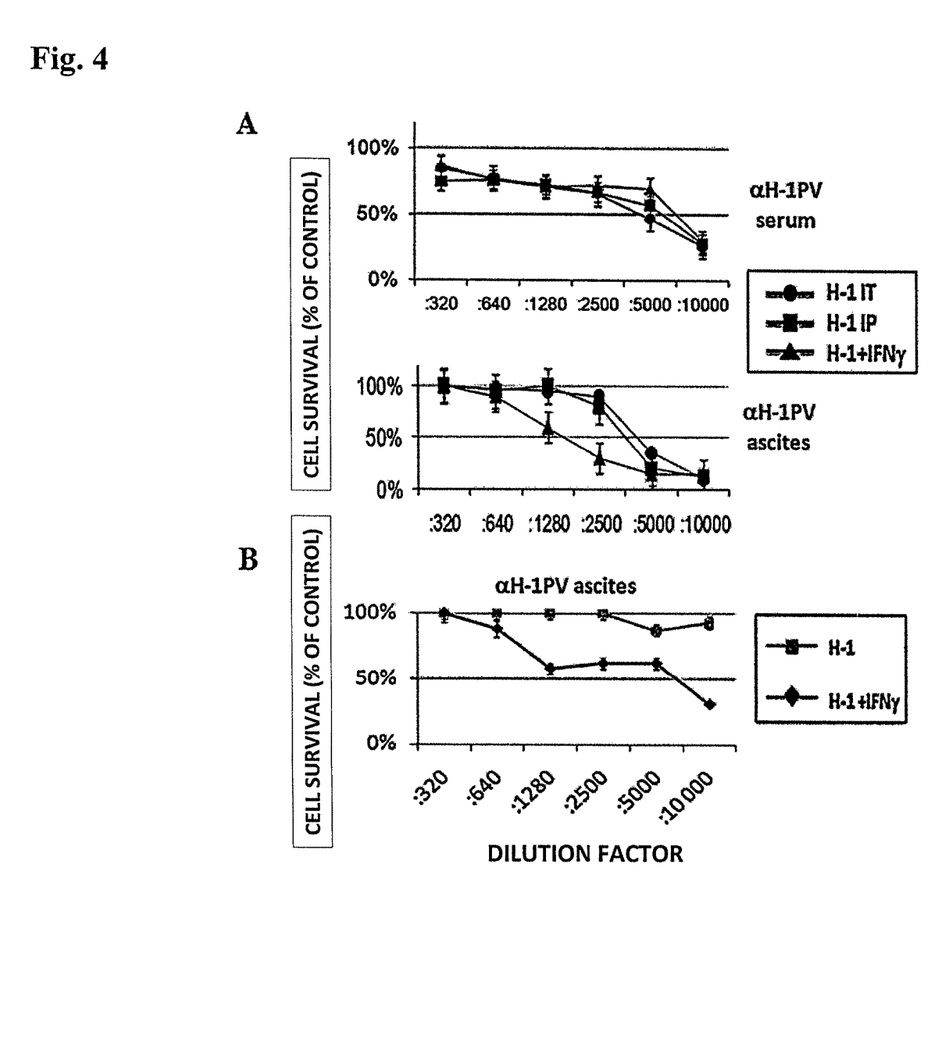
FIG. 4: Influence of $IFN_{\gamma}$ application on the generation of virus neutralizing antibodies (A) Serum and ascitic fluid were collected from all groups of virus-treated rats (see FIG. 2) and the titers of virus neutralizing antibodies (αH-1PV) were determined using cytotoxicity protection assay on NB324K cells. The titers are expressed as the percentage of antivirus protection offered by serum or ascitis dilutions compared to mock infected cells.

RecIFN$_Y$ Cotreatment Reduces the Titers of H-1PV Neutralizing Antibodies in Ascitic Fluid One of the major functions of IFN$_Y$ is its ability to prime the cellular (through Th1 cells/cytokines) and to downmodulate the humoral (through Th2 cells/cytokines) immune response. Therefore, it was assumed that the combination of IFN$_Y$ and oncolytic H-1PV may also reduce the titers of neutralizing antibodies produced against the virus. In order to address this hypothesis, serum from peripheral blood and ascitic fluid from the peritoneal cavity of rats participating in the above-mentioned experiment were collected and the titers of αH-1PV antibodies were determined, using a cytotoxicity protection assay on virus-sensitive cells. It was found that in the first experiment performed, no evident difference could be detected in the titer of αH-1PV in animal sera irrespective of the virus inoculation route and IFN$_Y$ treatment (FIG. 4A upper pannel). Similarly, the inoculation route had no impact on the antiviral titers in ascitic fluid collected in the time-frame (20 to 40 days) after virus treatment. On the other hand, co-application of recIFN$_Y$ together with H-1PV caused a significant reduction (from 1:5000 to 1:1280) in the titers of αH-1PV in the ascitic fluid of the animals most probably due to the stronger effect of i.p. applied IFN$_Y$.

Then, in a modified experimental setting it was tested whether the IFN$_Y$-provoked drop in antiviral antibodies within ascites would increase the levels of H-1PV DNA in metastases when this cytokine is applied before a second virus inoculation. First, it was noticed that the titers of αH-1PV in ascitic fluid collected within 10 to 30 days after this second H-1PV i.p. injection (FIG. 4B) were much higher than the ones induced by a single H-1PV i.p. application (FIG. 4A). This effect was most probably due to boosting of the immune system related to the repeated virus application. Interestingly, when IFN$_Y$ was applied before the second H-1PV inoculation (H-1+IFN$_Y$) it was noticed that αH-1PV titers remained similar to the ones observed in fluids from animals subjected to a single virus inoculation (compare FIG. 4B with FIG. 4A, lower panel), suggesting that the cytokine has inhibited the overproduction of αH-1PV triggered by the second virus injection.

The H-1PV transduction level of metastasis in the two groups of rats after the second virus application (SFIG. 1) was also evaluated. Unfortunately, IFN$_Y$ treatment had no positive impact on the amounts of viral DNA in metastasis despite the reduction of antiviral antibodies (FIG. 4B) suggesting that this reduction was not sufficient to overcome the antibody pressure in ascitic fluid.

EXAMPLE 5

Figure 5:
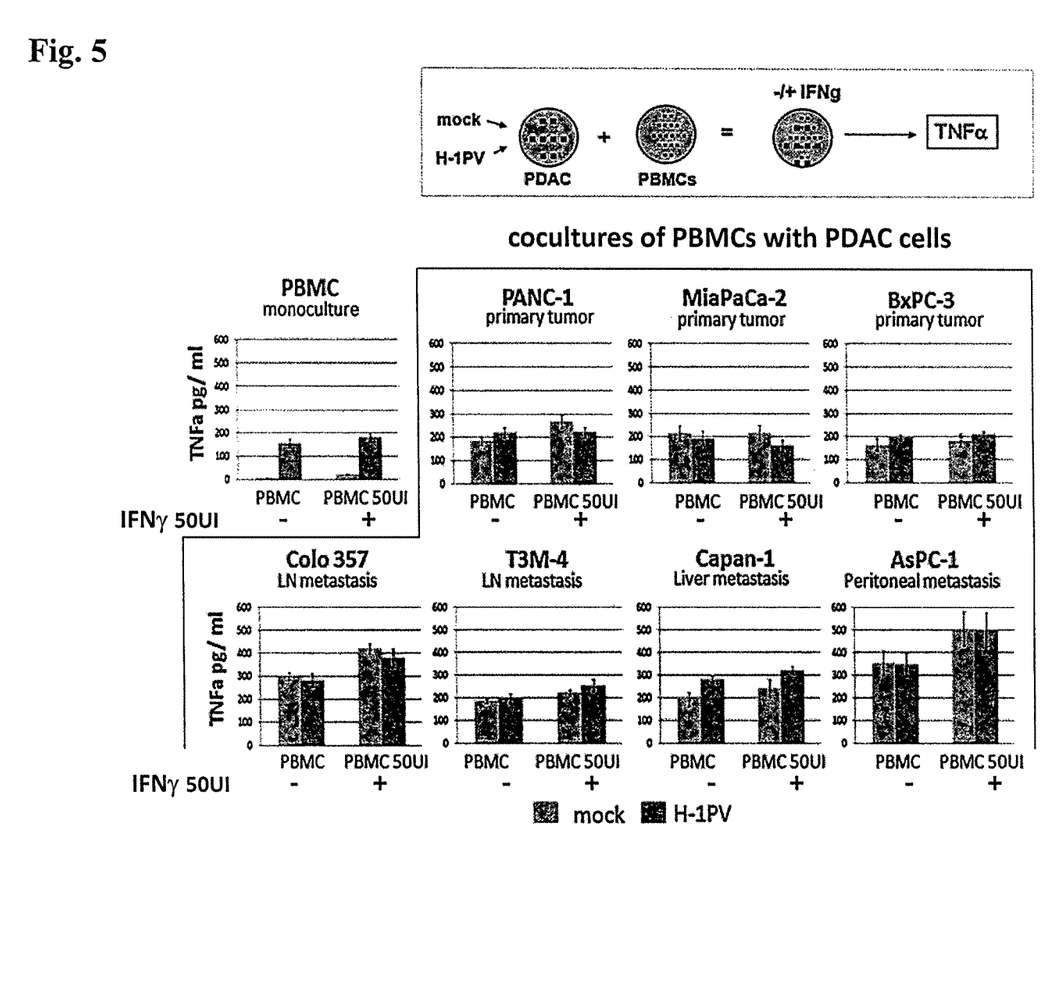
FIG. 5: Release of TNFα from PDAC and PBMC cocultures after H-1PV+$IFN_{\gamma}$ treatment The indicated pancreatic cancer cell lines were seeded into 10 cm² dishes at $1.5\times10^6$ cells/dish and infected or not with H-1PV at an MOI of 10 pfu/cell. 24 hpi cells were harvested and plated onto pre-isolated PBMCs in 48 well plates at a ratio of PDAC:PBMC 1:5. The cocultures were treated or not with 50 UI/ml of human recombinant $IFN_{\gamma}$ and the release of TNFα was measured in supernatants 24 hrs later by ELISA. Mock or H-1PV infected (MOI 10) monocultures of PBMCs served as controls. The indicated values are average of at least three independent experiments. SD values are shown.

Rec IFN$_Y$ Can Improve the Effect of H-1PV to Stimulate the Human Innate Immune System In search of clinical relevance of the obtained data, the previous studies were continued using human PDAC cell lines and peripheral blood monocytes derived from healthy donors, aiming to find out whether the latter can be activated more efficiently with a combination of virus and IFN$_Y$. It was previously reported that H-1PV infection leads to a limited but significant activation of human PBMCs as indicated by their TNFα release. The latter effect was largely masked in the case when PBMCs were cocultivated with pancreatic cancer cells irrespective of their infection status (6). Considering the fact that PDAC cells can express IFN$_Y$ receptors (12,13) first of all the lethal effect of H-1PV and IFN$_Y$ combination on pancreatic cancer cell was evaluated. IFN$_Y$ does not change H-1PV-induced toxicity on human PDAC cells (SFIG. 2). In a next step, PBMCs were cocultured with pancreatic cancer cells that had been previously infected (or not) with H-1PV, and used the release of TNFα as a read-out for innate immune cell activation. As already previously reported, the direct infection of PBMCs with H-1PV resulted in an increased release of TNFα at 48 hpi (FIG. 5, PBMC monoculture) (6). Addition of relatively low dose IFN$_Y$ (50 UI/ml) to the cultures did not significantly enhance TNFα production. The same was the case when PDACs were pre-infected with H-1PV before cocluturing them with the PBMCs. However, in general, in the presence of IFN$_Y$, PBMC cocultures with Panc-1, T3M4, Capan-1 and especially Colo357 and AsPC-1 produced 100-150 pg/ml more TNF$_Y$, corresponding to a higher level of activation of innate immune cells. Interestingly, despite the fact that the fluctuations of TNFα were not statistically significant, a tendency could be observed that PDAC cells deriving from metastatic (lymph node, liver or peritoneal) pancreatic cancer seemed to be more potent stimulators of PBMCs in the presence of IFN$_Y$ than the lines established from primary PDAC tumors. In general, all these effects support the hypothesis that concomitant application of IFN$_Y$ can be beneficial for the anticancer vaccination effect of H-1PV especially in the treatment of advanced metastatic disease.

CONCLUSION

The observed reduction in the titers of virus neutralizing antibodies induced by IFN$_Y$ represents a very interesting phenomenon in the frame of oncolytic virotherapy. It is in agreement with the changes observed in the I1-12/I1-10 cytokine ratio secreted from macrophages in the Th1/Th2 balance in the peritoneal cavity. Probably, an additional modification of the IFN$_Y$ treatment protocol or its combination with certain immunosuppressive agents, recently reported in oncolytic virotherapy may improve the described effect and reduce the antibodies to levels permitting repeated virus applications and metastasis transduction (7).

Treatment of peripheral blood mononuclear cells with H-1PV could prime the release of TNFα, a cytokine that represents one of the main products secreted upon macrophage activation possessing also strong antitumor properties. However, cocluturing PBMCs with pancreatic cancer cell lines deriving from different organ locations caused a generalized increase in TNFα levels that seemed to almost completely mask the effect of H-1PV pre-infection of PDAC cells. IFNy could serve as an additional stimulator of TNFα production mostly in the case of cocultures between PBMCs and metastatic PDAC cancer lines. Notably, this effect was most pronounced for AsPC-1, a cell line deriving from a clinical case of peritoneal metastasis, therefore giving stronger credibility to the results obtained in animal experiments with peritoneal carcinosis. In conclusion, the combination of an oncolytic virus with a powerful imunomodulating cytokine like $IFN_\gamma$ may represent a promising strategy for cancer therapy. In view of the forthcoming clinical applications of H-1PV as an oncolytic agent, a therapeutic protocol involving co-treatment with the two modalities has potential to improve the outcome in terminal stage patients with pancreatic cancer.

LIST OF REFERENCES

1. Ahmedin J, Siegel R, Ward E, Hao Y, Xu J and Thun M. Cancer Statistics 2009. CA Cancer J Clin 2009; 59:225-49.
2. Katz M H, Fleming J B, Lee J E, Pisters P W. *Current status of adjuvant therapy for pancreatic cancer*. Oncologist 2010; 15:1205-13.
3. Kim D H, McCormick F. Replicating viruses as selective cancer therapeutics Mol Med Today 1996:2:519-527.
4. Cornelis J J, Haag A, Kornfeld C et al. Autonomous parvovirus vectors In: Cid-Arregui A, Garcia-Garrancá A, eds *Viral Vectors: Basic Science and Gene Therapy Natick*, MA: Eaton Publishing 2000; 97-118.
5. Angelova A L, Aprahamian M, Grekova S P, Hajri A, Leuchs B, Giese N A, et al. *Improvement of gemcitabine-based therapy of pancreatic carcinoma by means of oncolytic parvovirus H-1PV*. Clin Cancer Res 2009; 15:511-9.
6. Grekova S, Aprahamian M, Giese N, Schmitt S, Giese T, Falk C S, et al. *Immune cells participate in the oncosuppressive activity of parvovirus H-1PV and are activated as a result of their abortive infection with this agent*. Cancer Biol Ther 2011; 10:1280-9.
7. Lun X Q, Jang J H, Tang N, Deng H, Head R, Bell J C, et al. Efficacy of systemically administered oncolytic vaccinia virotherapy for malignant gliomas is enhanced by combination therapy with rapamycin or cyclophosphamide. Clin Cancer Res 2009; 15:2777-88.

The invention claimed is:

1. A method of treating terminal stage pancreatic cancer characterized by peritoneal carcinosis in a patient suffering from a terminal stage pancreatic cancer that is characterized by peritoneal carcinosis, comprising administering to the patient an effective dose of a combination of parvovirus HI (H1-PV) and interferon-γ (IFN-γ), wherein said parvovirus is administered intratumorally and the IFN-γ is administered intraperitoneally, wherein the combination further comprises an immunosuppressive agent, further wherein said treatment increases survival of the patient suffering from terminal stage pancreatic cancer characterized by peritoneal carcinosis as compared to survival of a patient who has not received said treatment.

2. The method of claim 1, wherein the immunosuppressive agent is rapamycin or cyclophosphamide.

* * * * *